(12) United States Patent
Betz et al.

(10) Patent No.: US 6,245,075 B1
(45) Date of Patent: Jun. 12, 2001

(54) DISTRACTION DEVICE FOR MOVING APART TWO BONE SECTIONS

(75) Inventors: Augustin Betz, Constance; Michael Butsch, Daisendorf, both of (DE)

(73) Assignee: Wittenstein Motion Control GmbH, Igersheim (DE)

( * ) Notice: Subject to any disclaimer, the term of this patent is extended or adjusted under 35 U.S.C. 154(b) by 0 days.

(21) Appl. No.: 09/341,230

(22) PCT Filed: Jan. 7, 1998

(86) PCT No.: PCT/EP98/00060

§ 371 Date: Dec. 9, 1999

§ 102(e) Date: Dec. 9, 1999

(87) PCT Pub. No.: WO98/30163

PCT Pub. Date: Jul. 16, 1998

(30) Foreign Application Priority Data

Jan. 7, 1997 (DE) .............................. 197 00 225

(51) Int. Cl.[7] .............................. A61B 17/66; A61B 17/56

(52) U.S. Cl. .............................. 606/105; 606/90; 606/60

(58) Field of Search .............................. 606/60, 62, 63, 606/64, 65, 67, 68, 69, 72, 73, 74, 105, 90

(56) References Cited

U.S. PATENT DOCUMENTS

| | | | |
|---|---|---|---|
| 4,016,874 | * 4/1977 | Maffei et al. | 606/62 |
| 4,275,717 | * 6/1981 | Bolesky | 606/63 |
| 4,621,629 | * 11/1986 | Koeneman | 606/65 |
| 4,931,055 | * 6/1990 | Bumpus et al. | 606/60 |
| 4,940,467 | * 7/1990 | Tronzo | 606/66 |

(List continued on next page.)

FOREIGN PATENT DOCUMENTS

| | | |
|---|---|---|
| 2417233 | 10/1975 | (DE) . |
| 2713837 | 10/1978 | (DE) . |
| 2621175 | 4/1979 | (DE) . |
| 8515687 | 12/1985 | (DE) . |
| 3739059A1 | 5/1989 | (DE) . |

(List continued on next page.)

OTHER PUBLICATIONS

Soviet Inventions Illustrated, Sections P. Q: General/Mechanical, 1984, Week 8414, 84–087503/14 SU 1025–421–A.

Primary Examiner—Gene Mancene
Assistant Examiner—Michael B. Priddy
(74) Attorney, Agent, or Firm—Townsend and Townsend and Crew LLP

(57) ABSTRACT

The invention concerns a distraction device for moving apart two bone sections, in particular for extending bones or bridging a gap in a bone, the device comprising an intramedullary nail (1) which can be introduced into the medullary space of a bone and comprises two parts (2, 3) which can be moved axially and can each be secured to one of the two bone sections. The distraction device further comprises a drive unit (4) that drives a drive shaft (16), and a device for converting the rotational movement of the drive shaft (16) into a relative axial movement of the two parts (2, 3) of the intramedullary nail (1). In order to increase operational reliability and reduce the overall size of the device while retaining the high degree of efficiency, the drive shaft (16) drives planetary rollers (19) which are held on orbits on which they engage by means of drive grooves (21) provided on their outer periphery in corresponding drive grooves (8) in a hollow body (7) surrounding the planetary rollers (19), at least the drive grooves (8) of the hollow body (7) or of the planetary rollers (19) being designed as threaded grooves in order to displace the hollow body (7) axially relative to the drive shaft (16) when the latter is rotated.

25 Claims, 7 Drawing Sheets

U.S. PATENT DOCUMENTS

| | | | | |
|---|---|---|---|---|
| 5,057,103 | * | 10/1991 | Davis | 606/63 |
| 5,334,184 | * | 8/1994 | Bimman | 606/63 |
| 5,356,411 | * | 10/1994 | Spievack | 606/63 |
| 5,364,496 | * | 11/1994 | Robinson et al. | 606/53 |
| 5,415,660 | | 5/1995 | Campbell . | |
| 5,429,638 | * | 7/1995 | Muschler et al. | 606/60 |
| 5,505,734 | * | 4/1996 | Caniggia et al. | 606/63 |
| 5,540,687 | * | 7/1996 | Fairley et al. | 606/60 |
| 5,540,691 | * | 7/1996 | Elstrom et al. | 606/64 |
| 5,575,790 | * | 11/1996 | Chen et al. | 606/60 |
| 5,700,263 | * | 12/1997 | Schendel | 606/57 |
| 5,704,938 | * | 1/1998 | Staehlin et al. | 606/62 |
| 5,713,901 | * | 2/1998 | Tock | 606/62 |

FOREIGN PATENT DOCUMENTS

| | | |
|---|---|---|
| 8907561 | 1/1990 | (DE) . |
| 3921972A1 | 1/1991 | (DE) . |
| 19624295A1 | 1/1997 | (DE) . |
| 19625761A1 | 1/1997 | (DE) . |
| 19717357A1 | 2/1999 | (DE) . |
| 0346247B1 | 12/1989 | (EP) . |
| 0510840A1 | 10/1992 | (EP) . |
| 2053724 | 2/1996 | (RU) . |
| WO 96/25117 | 8/1996 | (WO) . |
| WO 97/03308 | 1/1997 | (WO) . |
| WO 97/25554 | 7/1997 | (WO) . |

* cited by examiner

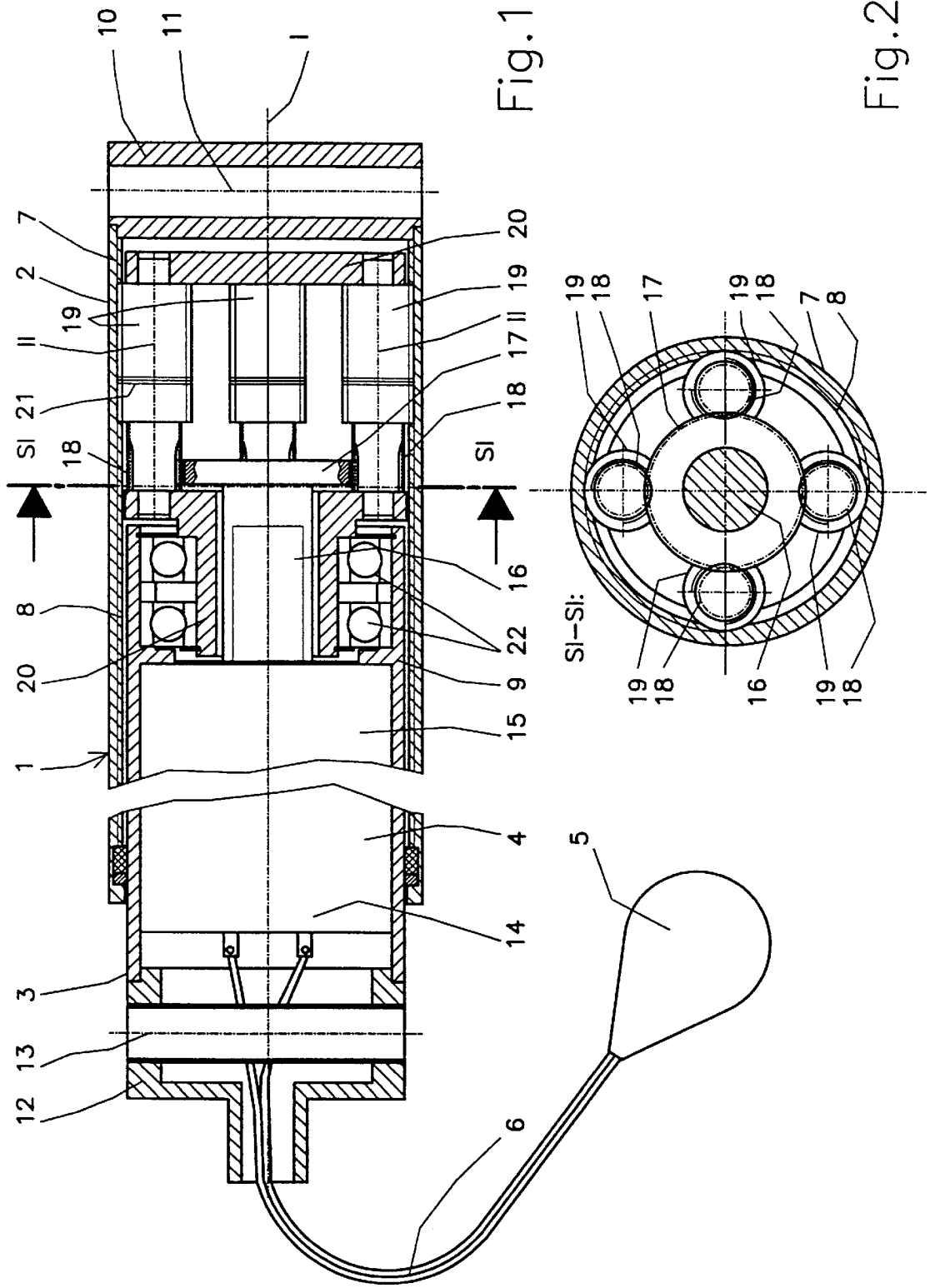

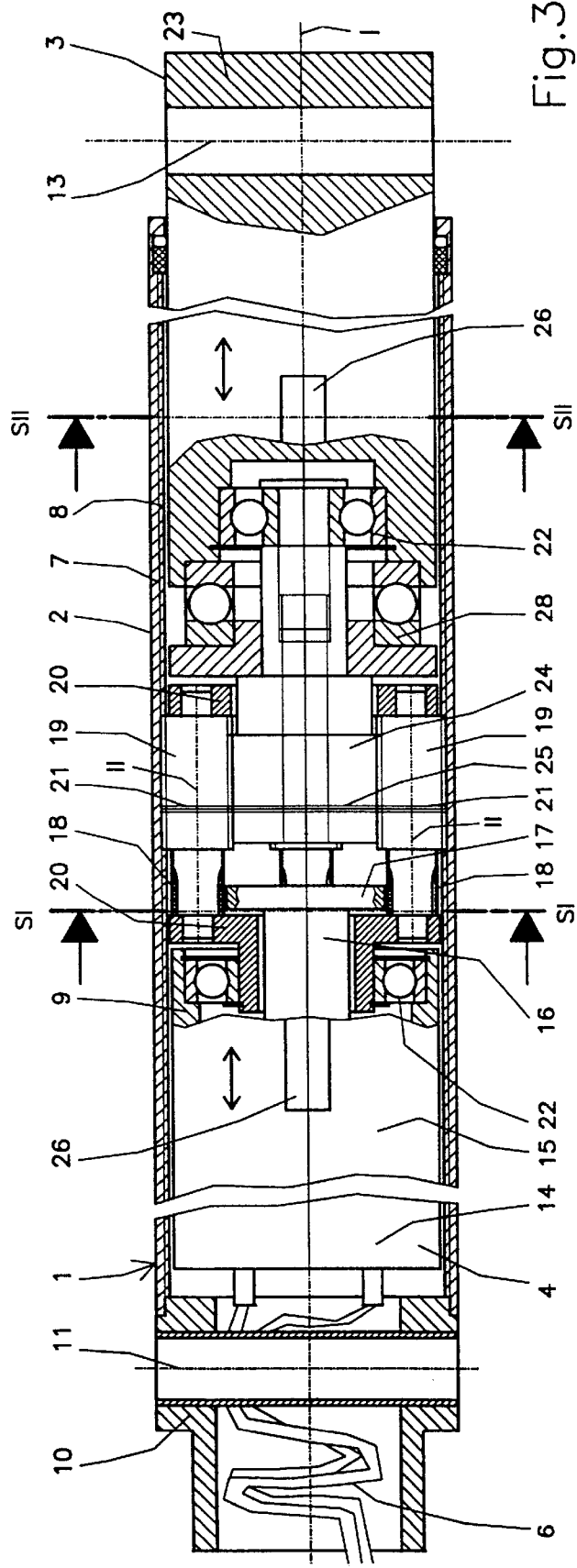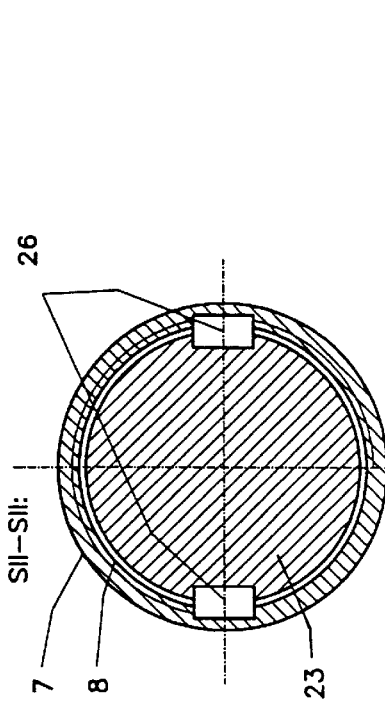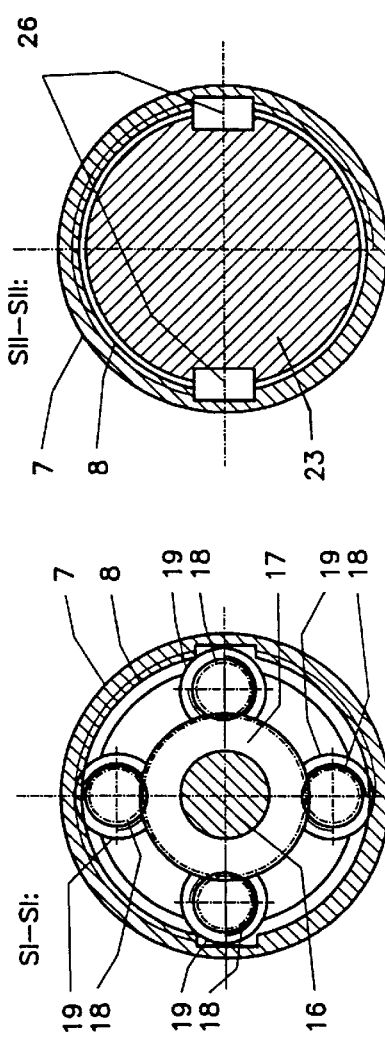

DISTRACTION DEVICE FOR MOVING APART TWO BONE SECTIONS

BACKGROUND OF THE INVENTION

The present invention relates to a traction apparatus for moving apart two parts of a bone, in particular for bone extension or to bridge a bone gap, comprising a medullary pin which can be introduced into the medullary space of a bone and which has two parts respectively securable to one of the two bone parts and moveable axially apart, a drive unit which drives a drive shaft and a device for converting the rotational movement of the drive shaft into a relative axial movement of the two parts of the medullary pin.

The use of a medullary pin as part of such a traction apparatus is known from document DE 39 21 972 C2. This apparatus serves in particular for the extension of tubular bones or the bridging of defects after comminuted fractures, or an inflammatory bone process or after the removal of tumors in the area of longer tubular bones. This known apparatus already has considerable advantages in comparison with external traction apparatuses in which the bone parts are connected outwardly through the skin to an adjustable frame, since through this a continuous danger of infection is present due to the entry of germs and also an unfavorable application of force is present.

The manner of operation of the known medullary pin is such that by moving the two parts of the medullary pin apart from one another the two parts of the bone can be moved slowly apart from one another, with the gap which thereby forms between the two bone ends continuously being bridged by newly forming bone substance as a result of the slow advance. In this manner bone can not only be extended in that bones are separated and subsequently drawn apart after drilling and insertion of the medullary pin into the medullary space, but rather bone gaps can also be bridged in that a bone piece separated from a bone end adjacent to the gap is moved from the one end of the gap to the other. Accordingly the end of a bone stub, i.e. a bone with a missing bone end, can also be extended.

Important in an apparatus of the initially named kind is that the movement of the bone parts apart from another takes place slowly in order to provide adequate time for the formation of bone substance and for the adaptation of the surrounding tissue.

SUMMARY OF THE INVENTION

The invention is based on the object of setting forth a traction apparatus of the initially named kind which is characterized by a high operational reliability which enables a constructional size which is as small as possible with at the same time a high degree of efficiency of the drive apparatus.

This object is satisfied in that the drive shaft drives planetary rollers which are held on orbits on which drive grooves on their outer circumference engage in corresponding drive grooves of a hollow body surrounding the planetary rollers, with at least the drive grooves of the hollow body or of the planetary rollers being formed as thread grooves in order, on a rotation of the drive shaft, to displace the hollow body axially relative to the latter.

The traction apparatus of the invention is characterized by a high degree of efficiency of its driving device. In this way a high operational reliability is ensured on the one hand and a small constructional size of the apparatus is made possible on the other hand, since the drive device can be made relatively small despite the high forces that are required. The traction apparatus of the invention is thus particularly suited for implantation into the body of the patient being treated.

For the driving of the planetary rollers the drive shaft is preferably provided with a pinion-like outer toothing which meshes into an outer toothing present at each planetary roller alongside the drive grooves. Another possibility lies in rotationally fixedly connecting the drive shaft to a cage rotatable in the hollow body and in which the planetary rollers are journalled. The second variant is simpler from the design viewpoint, but the transmission ratio of the gear stage is missing.

In accordance with a further design of the invention the hollow body surrounds the drive unit in telescope-like manner and forms a part of the medullary pin. This leads to a small constructional size of the traction apparatus, which can also be used with small and short bones as a result of the small length of the medullary pin which can be achieved thereby.

In accordance with further embodiments of the invention the drive unit can be fixed relative to one bone and the hollow body can be made extensible, or, however, the hollow body can be fixed to one bone and the drive unit with the planetary rollers and an axially loadable pin mounted coaxially to the hollow body can be extendible. The second variant has the advantage that the hollow body of larger diameter can be arranged in the proximal end of a tubular bone while the pin of smaller diameter can be arranged in the distal end, where less space is present. The loading by the introduction of the medullary pin is thereby reduced.

By providing a cardan joint between drive motor and hollow body the medullary pin can advantageously also be of hollow design. In particular a hollow body forming part of the medullary pin can be provided with bends.

Through the provision of a bend of the medullary pin the latter can be anatomically matched to the medullary space of a bone. The impairing of the bone by the traction apparatus is hereby reduced. Together with the small constructional size of the medullary pin made possible by the invention the medullary pin can also be designed so that it can be inserted into the medullary space of a medullary pin with out drilling open the bone substance. A weakening of the bone is hereby avoided, or at least reduced.

In accordance with a further design of the invention the hollow body drives the piston of a hydraulic pump by which the medullary pin can be driven. The drive device can in this manner be accommodated separately from the medullary pin and in particular implanted into the patient's body. This design also enables a design of the medullary pin with curvatures. It is advantageous in this respect to form the medullary pin as a piston-cylinder unit. One part of the medullary pin forms the piston which can be driven by the hydraulic pump.

In accordance with a further embodiment of the invention the drive unit includes an electric motor which can preferably be inductively supplied with energy, in particular by the coupling in of high frequency energy. In just the same way it is however also possible to drive the electric motor by an implantable energy store. In both cases it is ensured that no danger of infection exists through parts which are lead outwardly, for example connection wires of the traction apparatus.

In accordance with a further design of the invention a force measuring device and/or a path measuring device for the movement of the medullary pin and implantable in the body of the patient is provided. Through this measuring device the bone build-up process can be monitored and recorded without the patient having to be x-rayed and thus without the danger of a thereby produced burden for the patient.

In accordance with a further embodiment of the invention a strain gauge is provided as the force measuring device, whereas the path measuring device can for example operate potentiometrically. Another advantageous possibility lies in using an encoder adapted to the motor or a Hall sensor. The transmission of the measurement signals outwardly can for example take place by means of a telemetry system.

The determining parameters of the moving parts of the apparatus of the invention for the relationship between the speed of rotation of the drive shaft and the axial path of the hollow body can be summarized as follows in an equation resolved in accordance with the path of displacement:

$$S_{ax} = U_a \cdot \left( PS \cdot \frac{1}{d_{wa} + d_{wr}} - Pr \cdot \frac{d_{gs}}{d_{gr} \cdot d_{gr}} \right) \cdot \frac{d_{wa} \cdot d_{gr}}{d_{gr} + d_{wr}}$$

In this equation
$S_{ax}$=axial path of the hollow body
$U_a$=number of rotations of the drive shaft
Ps=pitch of the grooves of the hollow body
Pr=pitch of the grooves of the planetary rollers
$d_{gs}$=diameter of the grooves of the hollow body
$d_{gr}$=diameter of the grooves of the planetary rollers
$d_{wa}$=rolling circle diameter of the toothing of the drive shaft pinion
$d_{wr}$=rolling circle diameter of the toothing of the planetary rollers.

Using the above-cited equation a specific example will be given in the following:
$U_a$=1 revolution
Ps=1 mm
Pr=0
$d_{gs}$=10 mm
$d_{gr}$=$d_{wr}$=3 mm
$d_{wa}$=4 mm With the above values an axial path of displacement of the hollow body of $S_{ax}$=0.286 mm results for one revolution of the drive shaft.

In the case of a direct connection of the drive shaft and the cage with Pr=0:

$$S_{ax}=U_a \cdot Ps.$$

The planetary rollers can be without direct form-shaped and/or force-transmitting contact with the drive shaft in the region of their drive grooves. They can in particular be journalled in a freely rotatable cage which in turn is axially fixedly rollingly mounted on the housing of the drive shaft. The friction of the apparatus for the conversion of a rotary movement into an axial movement is thereby essentially and favorably reduced to rolling friction.

The cage can serve to guide the planetary rollers and to pick up the axial forces which originate from the planetary rollers. The axial forces of the planetary rollers can however also be directly taken up by the drive shaft. In this case the drive shaft is to be journalled as axially fixed to the drive housing.

For the transmission of the axial forces from the planetary rollers to the drive shaft the planetary rollers can be provided with bearing grooves in addition to their drive grooves, with the bearing grooves engaging into corresponding bearing grooves of the drive shaft in an axial force-supporting manner.

The counter-grooves or counter-sections engaging into the bearing grooves of the planetary rollers do not have to be a component of the drive shaft. They must simply be rotatably and axially fixed relative to the drive housing.

Fundamentally it is also possible for the drive grooves of the planetary rollers to simultaneously serve as their bearing grooves for the axial support on a rotating bearing body lying radially within the orbit of the planetary rollers.

In this case the bearing body can also be fixedly connected to the drive shaft with the drive grooves of the planetary rollers and also the bearing grooves of the bearing body then however each being of pitch-less design. Furthermore, with a design of this kind, the values of the average diameter of the grooves of the bearing body and of the rolling circle of the toothing between the drive pinion of the drive shaft and the planetary rollers should correspond.

The internal grooving of the hollow body can in particular be a multi-turn thread. With certain groove combinations of the rotatably interengaging parts of the drive apparatus a multi-turn thread is necessary, in particular with reference to the grooving of the hollow body.

The apparatus of the invention has the advantage that the hollow body can be extended in the form of a tube over a path on which previously no guide body must be present. Through the design as a tube the hollow body has a high buckling resistance. Moreover, the drive elements which lie within the tube can be simply and reliably sealed.

Embodiments of the invention are shown in the drawing and will be described in the following.

BRIEF DESCRIPTION OF THE DRAWINGS

FIG. 1 shows a traction apparatus in accordance with the invention in a partly sectioned representation with a contracted medullary pin, FIG. 2 is a cross-section in accordance with the line SI—SI in FIG. 1, FIG. 3 shows the medullary pin of a second variant of the traction apparatus of the invention in a partly sectioned representation, FIG. 4 is a cross-section in accordance with the line SI—SI in FIG. 3, FIG. 5 is a cross-section in accordance with the line SII—SII in FIG. 3.

DESCRIPTION OF THE PREFERRED EMBODIMENTS

Figure 6:
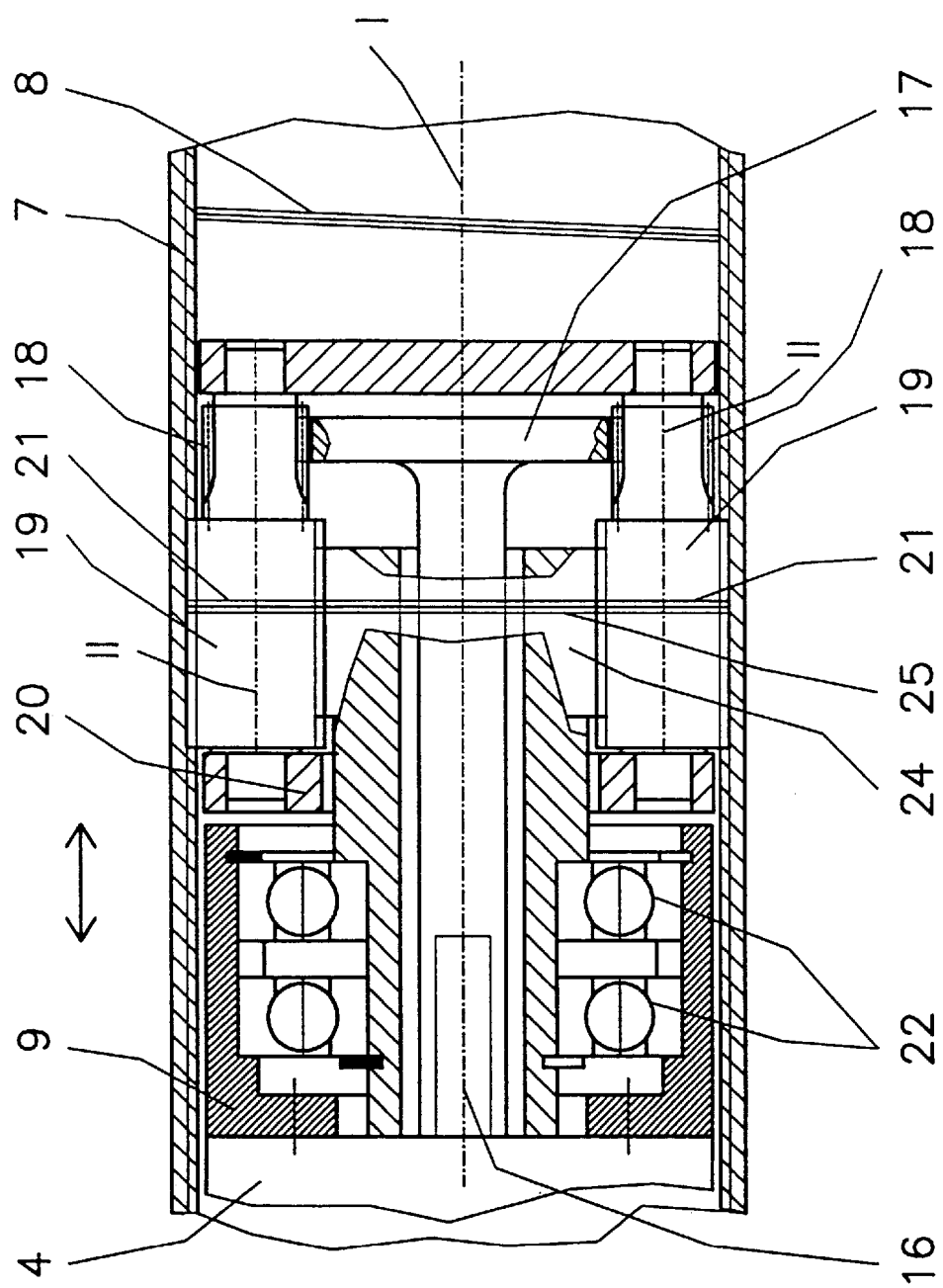
FIG. 6 is a section of a third variant of the traction apparatus of the invention.

The traction apparatus of the invention comprises a medullary pin 1 introduceable into the medullary space of a bone and having two axially extendible parts 2, 3 which are respectively securable to one of the two bone parts and also a drive unit 4 for driving apart the two parts 2, 3 of the medullary pin 1. The drive unit 4 is arranged in the interior of the medullary pin 1 and can be inductively supplied with energy from the outside via a coil 5, which can be implanted in the body of the patient, and electrical leads 6. An energy supply via an implanted battery would likewise be possible.

As one sees in FIG. 1 the first part 2 of the medullary pin 1 is formed by a tubular hollow body 7 which is provided at its inner peripheral surface with a grooving 8. The second part 3 of the medullary pin 1 is inserted into the one end of the tube 7 and likewise includes a tubular housing 9, while an end piece 10 is inserted into the other end of the tube 7. A through-opening 11 is present in the end piece 10 through which fastening means (not shown here), in particular a screw, can be introduced, with which the first part 2 of the medullary pin 1 can be secured to a bone or bone piece.

In the end of the housing 9 remote from the end piece 10 an end piece 12 is likewise inserted which is likewise provided with a through-opening 13 into which fastening means, in particular a fastening screw, can be introduced for the fastening of the second part 3 of the medullary pin 1 to a bone or bone piece. The electrical connection wires 6 which are fed in via the end piece 12 are connected to an electric motor 14 present in the interior of the housing 9. The electric motor 14 drives a drive shaft 16 via a transmission 15 which is likewise present in the housing 9, with the longitudinal axis of the drive shaft 16 coinciding with the longitudinal axis I of the medullary pin 1.

The drive shaft 16 is provided with a pinion-like toothing 17 which measures corresponding outer toothing 18 of four planetary rollers 19 which uniformly surround the pinion toothing 17 and are fixed by means of the cage 20, with the longitudinal axes II of the planetary rollers 19 extending parallel to the longitudinal axis I of the medullary pin 1.

The planetary rollers 19 are additionally provided with a grooving 21 of their outer side which stands in engagement with the grooving 8 on the inner peripheral side of the hollow body 7. The grooving 8 of the hollow body 7 is formed in this embodiment as a thread groove, i.e. thus has a pitch in the direction of the longitudinal axis I. In this manner a rotation of the drive shaft 16 transmitted by the pinion-like toothing 17 onto the planetary rollers 19 leads to a corresponding axial movement of the hollow body 7 while the planetary rollers 19 are axially fixed by the cage 20 relative to the drive shaft 16. The cage 20 can expediently be journalled relative to the housing 9 by rolling contact bearings 22.

The manner of operation of the medullary pin of the invention is such that the electric motor 14 supplied with energy via the induction coil 5 from outside of the body of the patient sets the drive shaft 16 rotating via the transmission 15 which in turn sets the planetary rollers 19 rotating via the pinion toothing 17 and the outer toothing 18. Through the rotation of the planetary rollers 19, which are axially fixed relative to the drive shaft 16, the hollow body 7 is extended as a result of the engagement of its grooving 8 with the grooving 21 of the planetary rollers 19. A bone piece secured to the hollow body 7 via the passage opening 11 is thereby moved away from a second bone piece which is connected via the passage opening 13 to the housing 9. The movement can take place very slowly and with very high force as a result of the high degree of efficiency of the drive device of the invention. The high degree of efficiency results above all from the fact that essentially only rolling friction and no sliding friction occurs between the moved elements of the medullary pin. New bone substance which closes the bone gap forms between the bone pieces which move apart from one another.

A bone can thus be extended in this manner. It is likewise possible to bridge an existing gap in a bone in that a bone piece separated from one end of the bone is moved to the other end of the gap. In this case it is also possible to use the apparatus of the invention so that the hollow body 7 is moved inwardly and not outwardly for the movement of the bone piece.

In the embodiments shown in FIGS. 3 to 8 and 11 the axial forces which act on the planetary rollers 19 are not picked up by the cage 20. In place of this a bearing body 24 is arranged with the planetary rollers and has a grooving 25 which engages in form-fitted manner into the grooving 21 or 27 respectively of the planetary rollers 19.

The variant shown in FIG. 3 is distinguished from the variant of FIG. 1 additionally by the fact that here the hollow body 7 can be fixed to the bone whereas, on actuation of the apparatus, the drive unit 4 with the drive shaft 16, planetary rollers 19, bearing body 24 and an axially loadable pin 23, which is connected via thrust-bearing 28 to the bearing body 24, is extended axially. Fitting pieces 26 present between the two parts 2 and 3 of the medullary pin 1 and extending in its longitudinal direction ensure in this arrangement a rotationally fixed fixation of the two parts 2 and 3 relative to one another. The pin 23 can be secured via the passage opening 13 to a bone piece which is to be displaced during the extension.

In the variant shown in FIG. 6 the drive shaft 16 passes through the bearing body 24. The pinion toothing 17 is arranged on the side of the drive shaft 16 remote from the drive unit 4. The bearing body 24 which picks up the axial forces is journalled via rolling contact bearing 22 relative to the housing 9.

Figure 7:
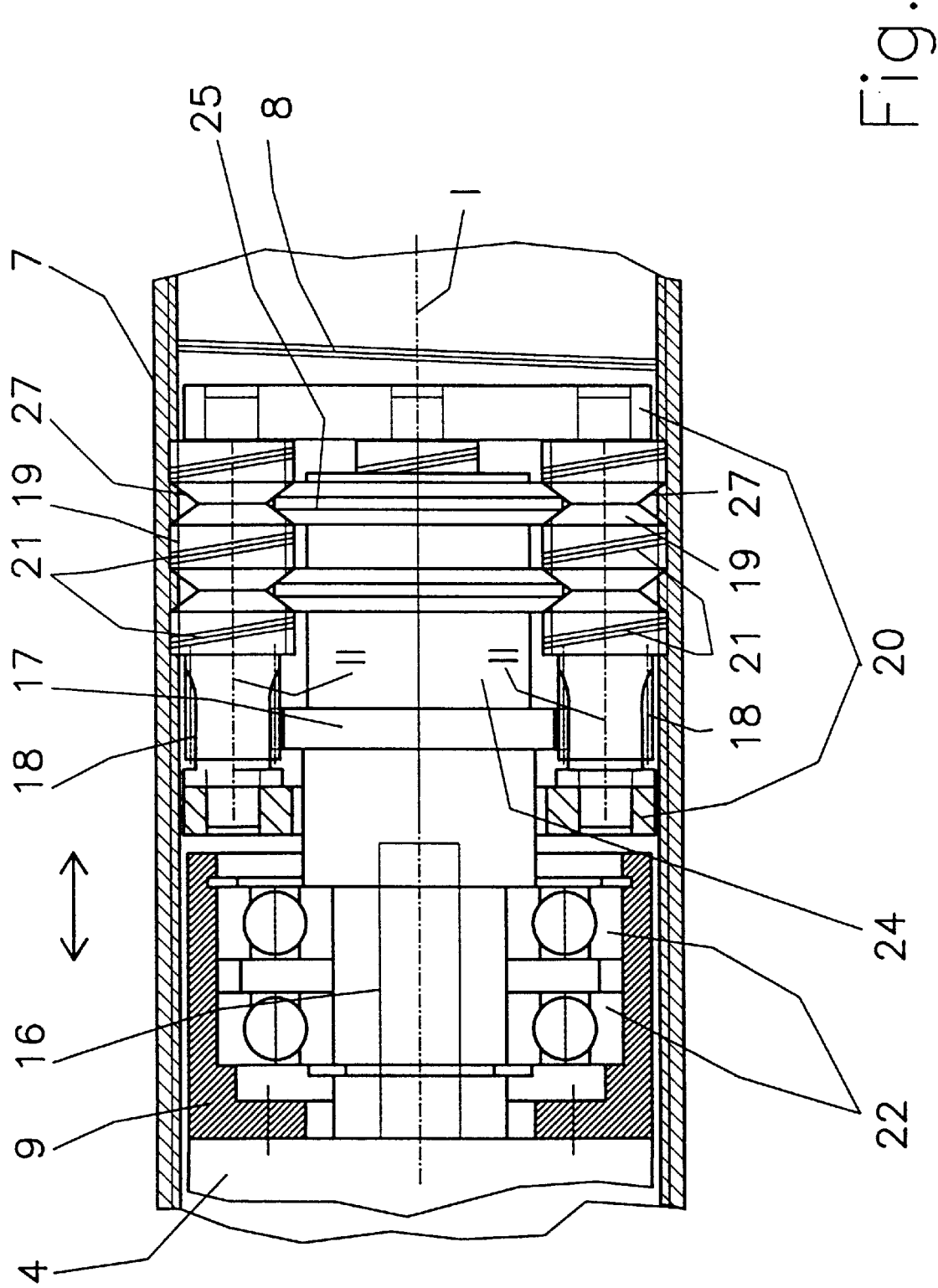
FIG. 7 is a section of a fourth variant of the traction apparatus of the invention.

The embodiment shown in FIG. 7 is distinguished from the embodiments shown in FIGS. 3 and 6 in that the planetary rollers 19 have two different groovings 21 and 27 of which the grooving 21 stands in engagement with the grooving 8 of the hollow body 7 whereas the grooving 27 engages into the grooving 25 of the bearing body 24. In this manner the grooving 21 of the planetary rollers 19 can also be formed with a pitch whereas the grooving 27 has no pitch as does the grooving 25 of the bearing body 24 in order to axially fix the planetary rollers 19 relative to the drive shaft 16.

Figure 8:
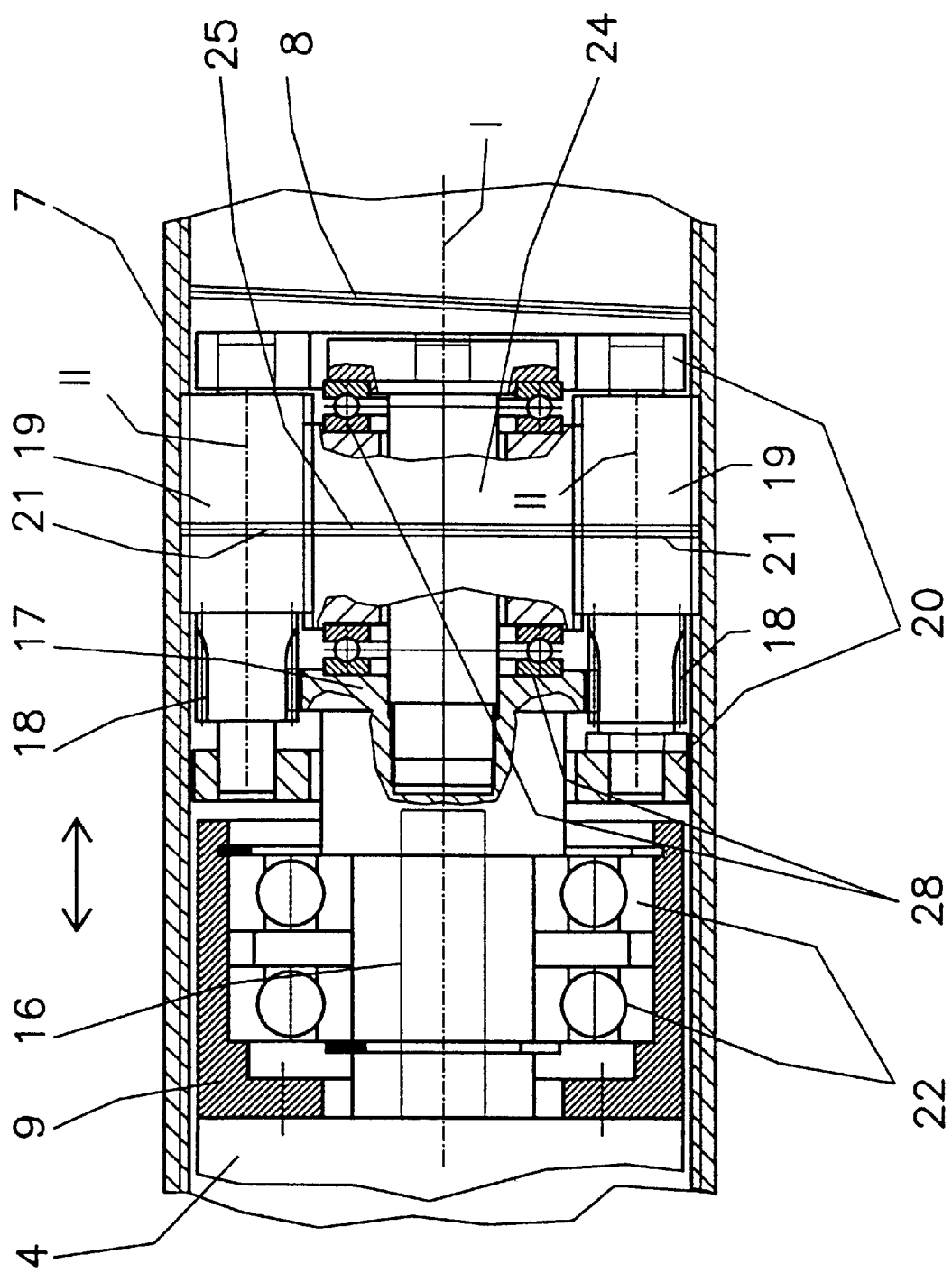
FIG. 8 is a section of a fifth variant of the traction apparatus of the invention.

The design of FIG. 8 is distinguished from the designs of FIGS. 3, 6 and 7 in that the bearing body 24 is admittedly axially fixed relative to the drive shaft 16 but is however freely rotatably mounted. For this purpose two thrust bearings formed as ball roller bearings are provided of which a respective one is provided at each of the two end faces of the bearing body 24. As a result of this design the rolling circle diameter of the pinion toothing 17 of the drive shaft 16 can be selected independently of the average diameter of the bearing grooves 25 of the bearing body 24.

Figure 9:
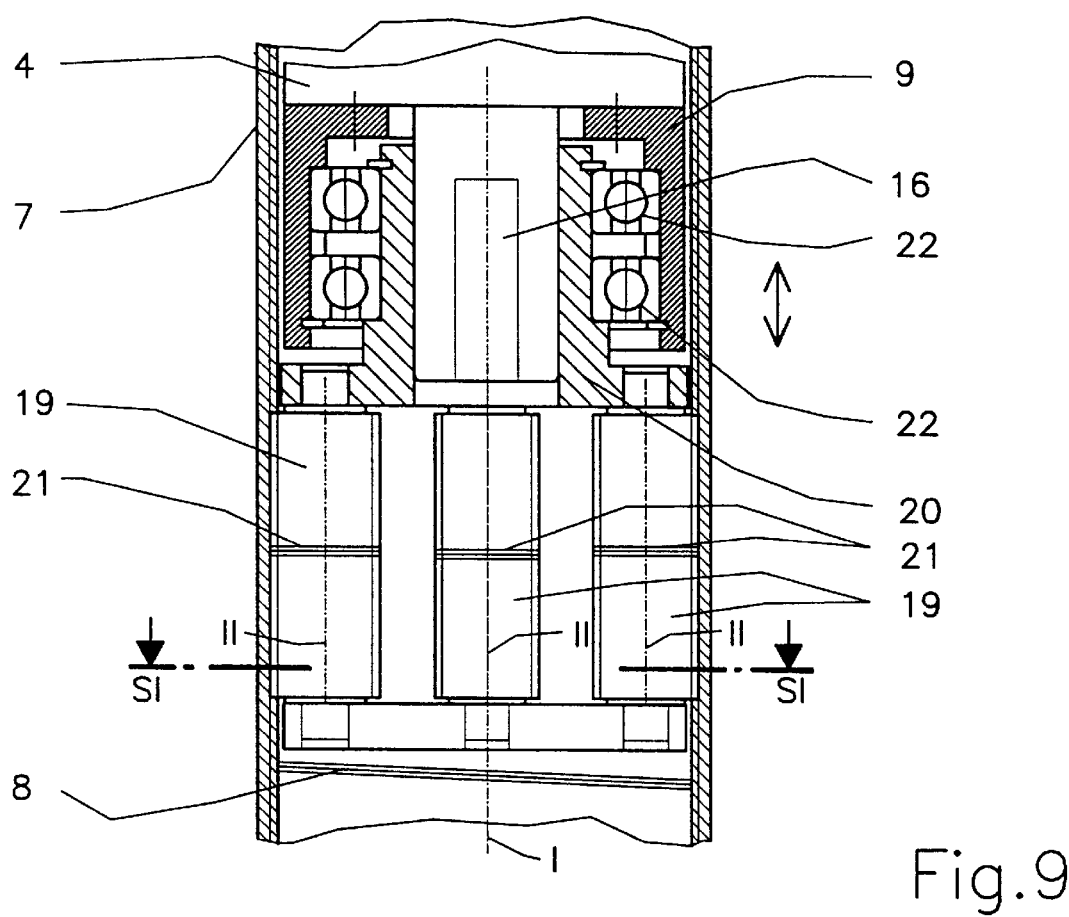
FIG. 9 is a section of a sixth variant of the traction apparatus of the invention.
Figure 10:
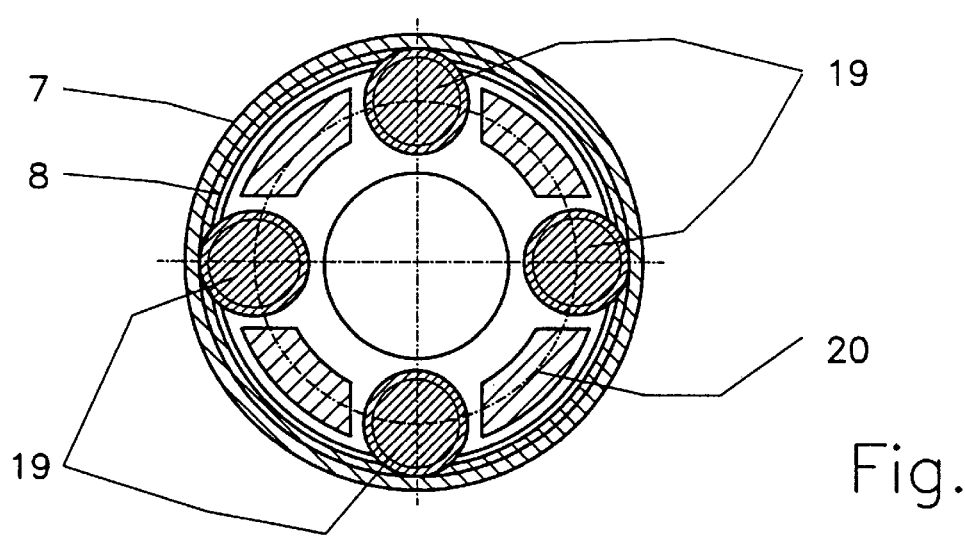
FIG. 10 is a cross-section in accordance with the line SI—SI in FIG. 9.

In the variant shown in FIG. 9 the drive shaft 16 is directly connected to the cage 20 of the planetary rollers 19 which are thus only provided with a grooving 21 but not with any outer toothing. The planetary rollers are thus moved via the cage along their orbits. The axial forces are directed from the cage 20 via the rolling contact bearings 22 onto the housing 9.

Figure 11:
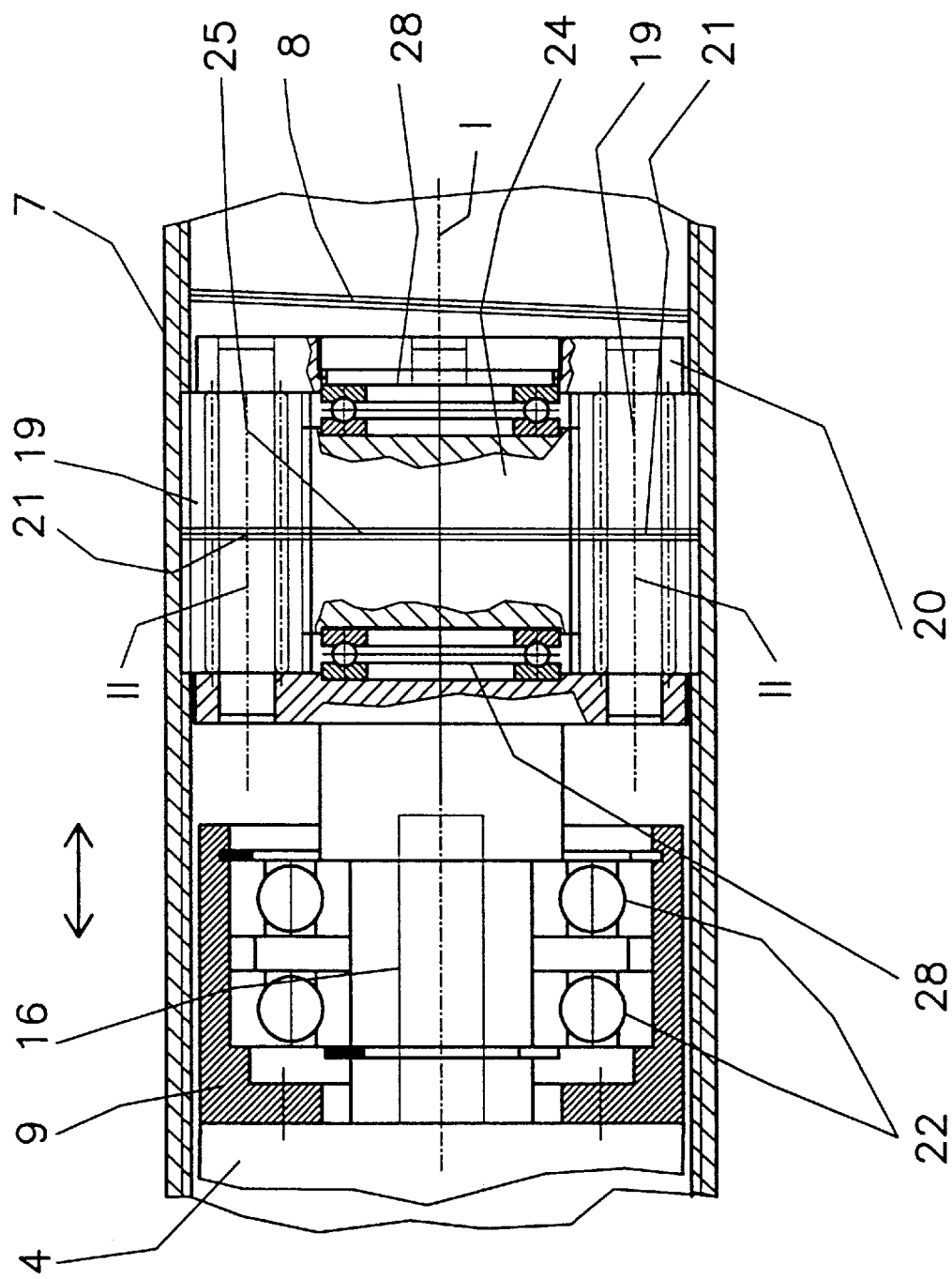
FIG. 11 is a section of a seventh variant of the traction apparatus of the invention.

FIG. 11 shows a design in which, as in the variant of FIG. 9, the cage 20 of the planetary rollers 19 is directly driven. The support of the axial forces takes place via a bearing body 24 the grooving 25 of which stands in form-fitted engagement with the grooving 21 of the planetary rollers 19. The bearing body 24 is supported via thrust-bearings 28 on the drive shaft 16 which is in turn journalled in the housing 9 via the rolling contact bearings 22.

The pinion toothing 17 or the cage 20 can in all cases also be cardanically driven via a coupling, so that a pivot angle can be realized between the drive shaft 16 and the axis of the hollow body 7.

What is claimed is:

1. A traction apparatus for moving apart two parts of a bone of a patient comprising a medullary pin which can be placed into a medullary space of a bone and which has two parts, respectively securable to one of the two bone parts, which can be moved axially apart, a drive unit for driving a drive shaft and a device for converting rotational movement of the drive shaft into a relative axial movement of the two parts of the medullary pin, and planetary rollers driven by the drive shaft and held in orbits on which drive grooves on their outer circumference engage corresponding drive grooves of a hollow body surrounding the planetary rollers, at least the drive grooves of one of the hollow body and the planetary rollers being formed as thread grooves so that, on a rotation of the drive shaft, the hollow body is displaced axially relative to the latter.

2. A traction apparatus in accordance with claim 1, wherein the drive shaft is provided for the driving of the planetary rollers with a pinion-like outer toothing which meshes in an outer toothing formed in each planetary roller alongside the drive grooves.

3. A traction apparatus in accordance with claim 1, wherein the drive shaft is rotationally fixedly connected to a cage that is rotatable in the hollow body and in which the planetary rollers are journalled for the driving of the planetary rollers.

4. A traction apparatus in accordance with claim 1, wherein the hollow body telescopically surrounds the drive unit and forms a part of the medullary pin.

5. A traction apparatus in accordance with claim 4, wherein the drive unit can be fixed relative to a bone and the hollow body is extendable.

6. A traction apparatus in accordance with claim 4, wherein the hollow body can be fixed on one bone and the drive unit with the planetary rollers, and wherein an axially loadable pin mounted coaxially to the hollow body is extensible.

7. A traction apparatus in accordance with claim 1, including a cardan joint between drive unit and hollow body.

8. A traction apparatus in accordance with claim 1, wherein the hollow body drives a piston of a hydraulic pump by which the medullary pin can be driven.

9. A traction device in accordance with claim 8, wherein the drive and the hydraulic pump are implantable in the body of the patient.

10. A traction apparatus in accordance with claim 1, wherein the drive unit includes an electric motor.

11. A traction apparatus in accordance with claim 10, wherein the electric motor can be supplied with energy inductively by coupling in high frequency energy.

12. A traction apparatus in accordance with claim 10, including an implantable energy store for driving the electric motor.

13. A traction apparatus in accordance with claim 1, including a device implantable into the body of the patient for measuring movements of the medullary pin.

14. A traction apparatus in accordance with claim 13, wherein the measuring device includes a strain gauge.

15. A traction apparatus in accordance with claim 13, wherein the device operates potentiometrically.

16. A traction apparatus in accordance with claim 13, wherein the device comprises an encoder adapted to the motor for measuring the length of medullary pin movements.

17. A traction apparatus in accordance with claim 13, including a Hall sensor for registering the number of rotations of the drive shaft.

18. A traction apparatus in accordance with claim 13, including a telemetry system for transmitting measurement signals out of the body of the patient.

19. A traction apparatus in accordance with claim 1, wherein in a region of their drive grooves the planetary rollers are not in force transmitting contact relative to the drive shaft.

20. A traction apparatus in accordance with claim 1, wherein the planetary rollers are journalled in a rotatable cage which is axially fixedly rollingly journalled on a housing of the drive shaft.

21. A traction apparatus in accordance with claim 1, including additional bearing grooves in the planetary rollers with which the planetary rollers are axially fixed in corresponding axially immovable counter-bearing grooves.

22. A traction apparatus in accordance with claim 21, wherein the bearing grooves of the planetary rollers engage axially non-displaceable counter-bearing grooves of a bearing body rotating on an axis of the drive shaft.

23. A traction apparatus in accordance with claim 22, wherein the bearing body is fixedly connected to the drive shaft, and wherein the bearing grooves of the planetary rollers and of the bearing body are each pitch-free.

24. A traction apparatus in accordance with claim 23, wherein values of an average diameter of the bearing grooves in the bearing body and of a rolling circle diameter in the toothing between the drive pinion and the planetary rollers correspond.

25. A traction apparatus in accordance with claim 22, wherein the bearing body is axially fixed and rotatably mounted on the drive shaft.

\* \* \* \* \*